United States Patent
Ellsworth et al.

(10) Patent No.: US 7,520,402 B2
(45) Date of Patent: Apr. 21, 2009

(54) STERILE DISPOSABLE UNIT

(75) Inventors: James R. Ellsworth, Marshfield, MA (US); Paul McGovern, Hanson, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 641 days.

(21) Appl. No.: 10/528,236

(22) PCT Filed: Sep. 17, 2003

(86) PCT No.: PCT/US03/29232

§ 371 (c)(1), (2), (4) Date: Mar. 18, 2005

(87) PCT Pub. No.: WO2004/026709

PCT Pub. Date: Apr. 1, 2004

(65) Prior Publication Data

US 2005/0247715 A1    Nov. 10, 2005

Related U.S. Application Data

(60) Provisional application No. 60/411,770, filed on Sep. 19, 2002.

(51) Int. Cl.
*B65D 25/04* (2006.01)

(52) U.S. Cl. .................................................. 220/501

(58) Field of Classification Search ................ None
See application file for complete search history.

(56) References Cited

U.S. PATENT DOCUMENTS

| | | | | | |
|---|---|---|---|---|---|
| 417,082 | A | * | 12/1889 | Pichereau | 211/69.2 |
| 2,784,434 | A | * | 3/1957 | Little | 401/122 |
| 3,508,653 | A | * | 4/1970 | Coleman | 210/789 |
| 5,172,826 | A | | 12/1992 | Celaya | |
| 5,341,953 | A | | 8/1994 | Forester | |
| 5,676,275 | A | | 10/1997 | Khattar | |
| 5,707,331 | A | | 1/1998 | Wells | |
| 5,878,908 | A | | 3/1999 | Foley | |
| RE38,757 | E | * | 7/2005 | Wells et al. | 494/20 |

FOREIGN PATENT DOCUMENTS

WO    WO 01/18396    3/2001

* cited by examiner

*Primary Examiner*—Stephen Castellano
(74) *Attorney, Agent, or Firm*—Clark & Brody

(57) ABSTRACT

A container designed for use as a disposable processing unit in a centrifuge includes first and second chambers connected by a bridge that allows transfer of fluid between the chambers. One of the chambers has a sloped floor that directs fluids to a smaller bottom portion for providing greater depth in the collected fluids. The container also includes cam surfaces that facilitate insertion of the container in a centrifuge in the desired orientation. As well, a key may be provided to ensure that the container is used in the correct centrifuge.

7 Claims, 5 Drawing Sheets

US 7,520,402 B2

STERILE DISPOSABLE UNIT

CROSS REFERENCE TO RELATED APPLICATIONS

This is a National Phase Entry of PCT/US03/29232 filed Sep. 17, 2003, which claims the benefit of U.S. Provisional Application Ser. No. 60/411,770 filed on Sep. 19, 2002.

TECHNICAL FIELD

This invention relates to the art of containers for use in treating fluids in a centrifuge. In particular, the invention relates to a disposable container having multiple chambers for processing blood and other physiological products in a centrifuge.

BACKGROUND

A decanting centrifuge using multi-chamber containers is known from U.S. Pat. No. 5,707,331. According to that patent, a sterile processing disposable provides two chambers arranged adjacent each other so that a supernatant in one of the chambers may be decanted to the other of the chambers by gravity draining or centrifugal transfer techniques.

SUMMARY OF THE INVENTION

In accordance with the invention, a sterile processing disposable unit provides features that facilitate separation of fluids and ease of manufacture. The container comprises a base portion and a lid, both of which can be inexpensively molded, as by injection molding. The base portion comprises two chambers having a partition therebetween. The partition preferably comprises spaced walls connected at their tops, but it may be a single wall. The top of the partition is configured to allow supernatant fluids to flow over it and into the adjacent chamber.

The size of each chamber is designed to accommodate the fluids to be received in the particular chamber and to facilitate centrifugal separation of the components of the material in the chamber. One chamber is generally tubular and of a size to receive a predetermined volume of blood to be processed to produce autologous platelet rich plasma of desired concentration. In preferred embodiments, this chamber is designed to receive 25 ml of blood in one case and 60 ml in another. The second chamber, which receives decanted plasma, may be smaller than the first chamber and further provides a still smaller bottom portion for receiving platelets separated from the decanted plasma to facilitate aspiration of these platelets. Preferably the cross section of the bottom portion is reduced to provide increased height of the platelets to further facilitate their aspiration.

The floor of the second chamber is preferably tapered to direct the separated platelets toward the bottom portion of the chamber so that they may be easily removed in a later step. In the preferred embodiment, the general configuration of the container is circular, and the tapered floor of the second chamber is preferably helical.

The helical configuration of the floor may also serve to orient the container in a centrifuge frame that receives the container. The frame is pivotally mounted to the centrifuge rotor by trunnions, and the helical floor of the container when not oriented will engage a part of the frame, such as an orienting projection on the side of the frame, as the user inserts the container in the frame. In the preferred embodiment, a skirt extends downward from the bottom surface to form a cam surface that engages the frame to orients the container in the frame during insertion. The skirt may be configured to provide the cam surface, and the inside floor of the chamber may have the same shape as the shirt or a different shape. This allows the floor of the second chamber to be configured to facilitate movement of the platelets toward the bottom portion of the chamber and the skirt to be configured to facilitate orientation of the container.

The container is also provided with exterior features that ensure the container is properly engaged in the frame. For example, the frame may be provided with a key that cooperates with a key on the container to ensure that the container is properly received in the frame. Further, the frame of a particular centrifuge may differ from that of another centrifuge to ensure that a container designed specifically for one centrifuge is not accidentally used with another centrifuge.

The bottom portion of the second chamber is preferably configured to accommodate the orientation of the container when in the decanting orientation and in the orientation assumed during a second centrifugation whereby platelets are separated from the decanted plasma.

The lid for the container covers the base portion to provide sterility while allowing sterile access to the chambers. The lid, thus, includes a sterile access port for each chamber, and a vent for allowing egress of air displaced during introduction of blood into the first chamber and ingress of air during withdrawal of plasma and/or platelets from the second chamber.

The container also includes a floating divider that is received in the first chamber. The floating divider is designed to assume a position at or near the interface between plasma and red blood cells, which have been separated during an initial centrifugation process. The floating divider is cup-shaped and designed to provide a space between its periphery and the interior of the first chamber to allow passage of plasma, red blood cells, and other cellular components during centrifugation. The preferred divider also includes a central opening to allow passage of components during centrifugation. During decanting, the divider tilts about an axis transverse to the longitudinal axis of the chamber and thereby acts as a valve that stops decant of red blood cells that lie below the divider.

DETAILED DESCRIPTION OF THE PREFERRED EMBODIMENT

Figure 1:
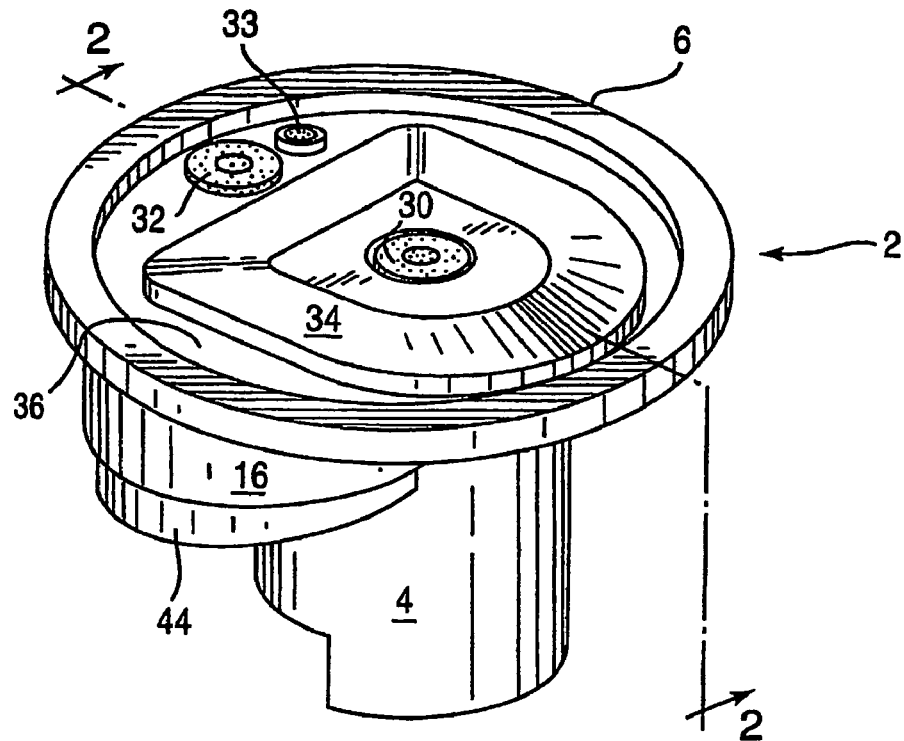
FIG. 1 is a perspective of a container in accordance with the invention.
Figure 2:
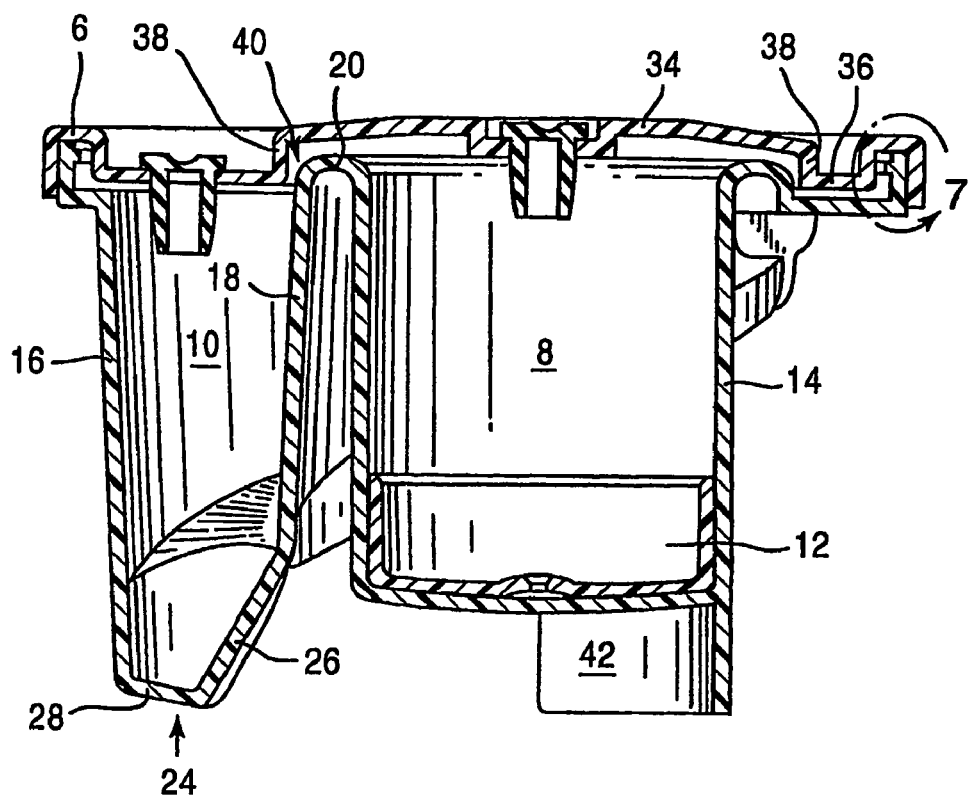
FIG. 2 is a cross section taken along line 2-2 of FIG. 1.

With reference to the figures, a preferred container 2 in accordance with the invention generally includes a base portion 4 and a lid 6. The base portion provides a first chamber 8 and a second chamber 10. The first chamber 8 is preferably cylindrical and formed by cylindrical outer wall 14, but may have other shapes. The first chamber receives a floating divider 12 that floats in the fluids to be introduced into the first chamber, and in the preferred embodiment, the divider 12 is cylindrical as well. It will be appreciated that the configuration of the first chamber must cooperate with that of the divider to allow the divider to float in the fluids.

Several walls intersect to provide the desired shape for the second chamber 10. A first outer wall 16 is generally cylindrical and extends at least partially around the first chamber 8. An inner wall 18 is also generally cylindrical and is joined to the outer wall 14 of the first chamber at their upper ends by a bridge portion 20.

Figure 3:
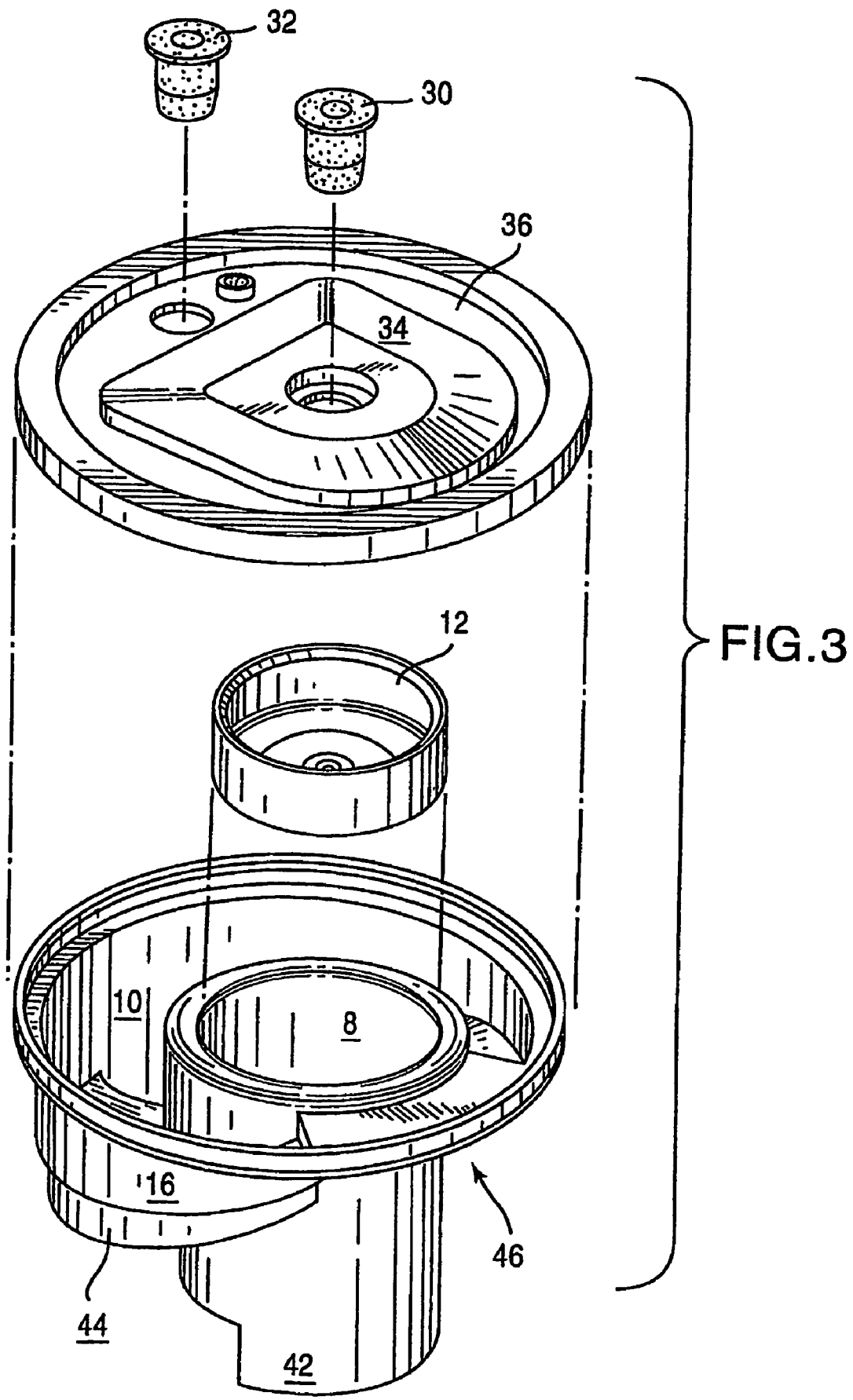
FIG. 3 is an assembly view of the container of FIG. 1.
Figure 4:
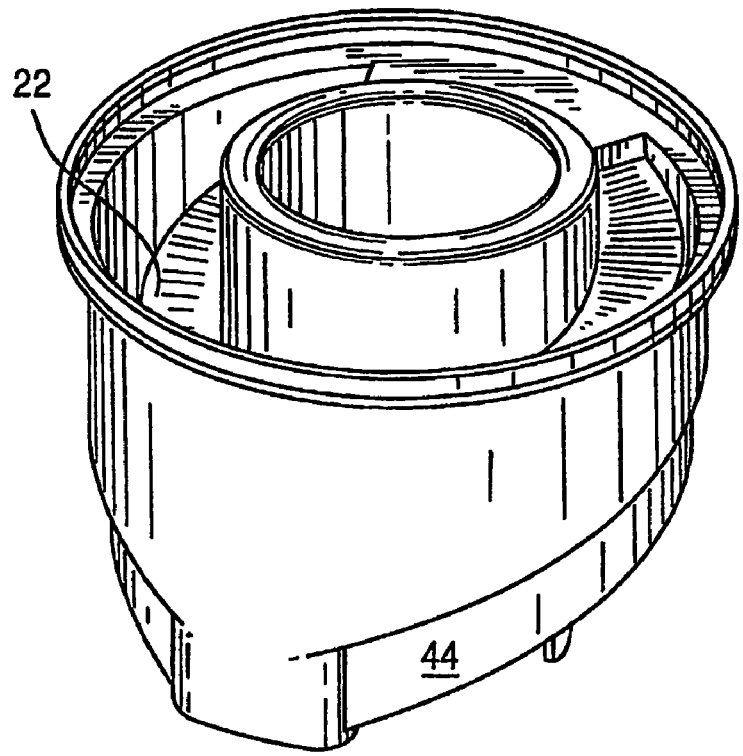
FIG. 4 is a perspective of the base portion of the container of FIG. 1.
Figure 5:
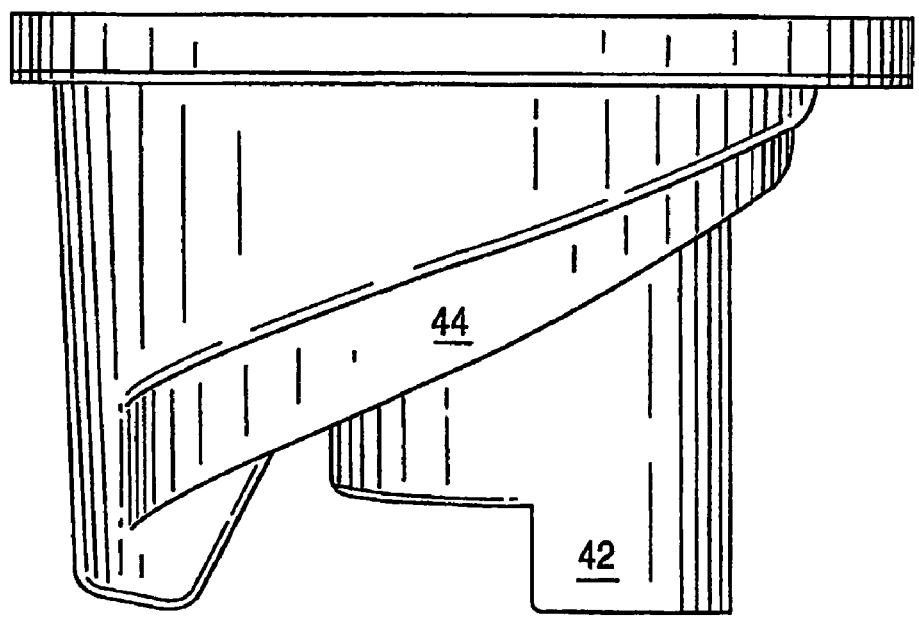
FIG. 5 is a side view of the base portion of FIG. 4.
Figure 6:
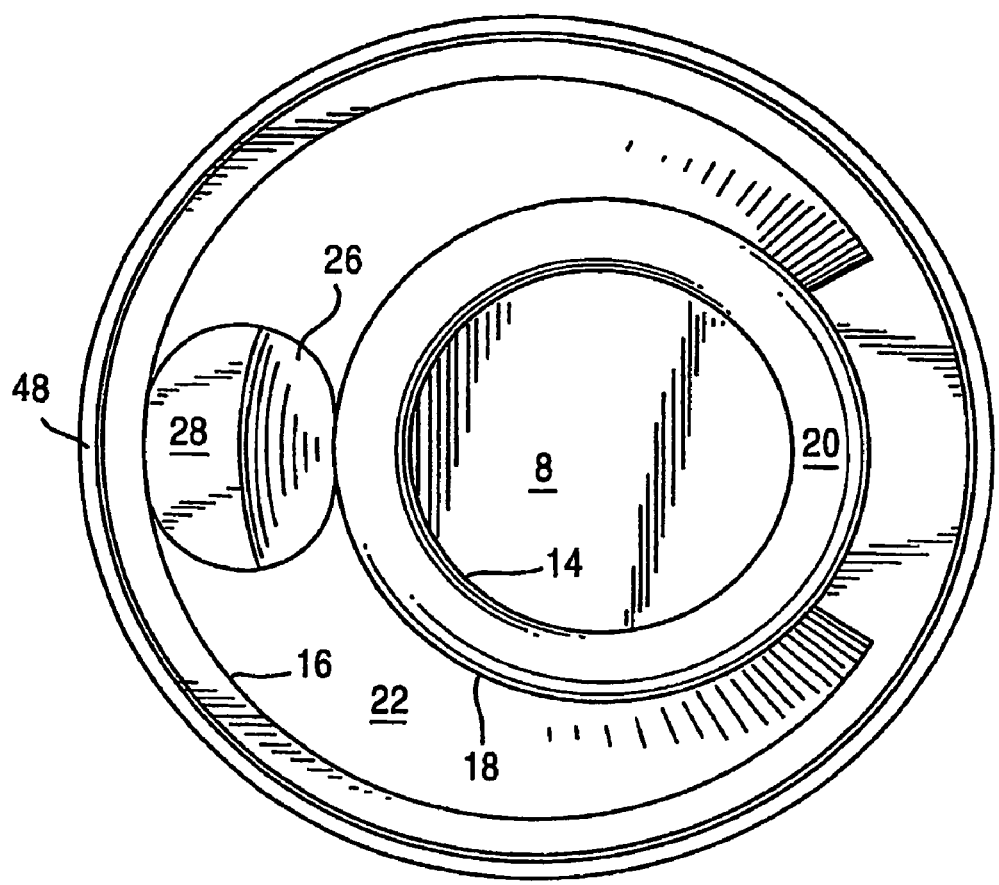
FIG. 6 is a top view of the base portion of FIG. 4.

The second chamber 10 includes a first floor portion 22 (see FIGS. 3, 4, 6) that is arranged to slope toward a bottom portion 24 of the second chamber. Floor 22 is preferably helical. The bottom portion includes surfaces 26 and 28 that further reduce the cross section of the bottom portion. It will be appreciated that the helical surface 22 directs platelets separated by centrifugation toward the bottom portion, and the reduced cross section of the bottom portion results in a reduced volume that provides greater vertical extent of the collected platelets to facilitate their removal from the second chamber by a cannula.

In the preferred embodiment, the surface 28 is oriented such that it is vertical when the container is subjected to centrifugation during collection of the platelets. For example, the bottom may be oriented at approximately 7° with respect to the upper surface of the base portion.

The lid 6 includes first access port 30 to provide sterile access to the first chamber and second access port 32 that provides sterile access to the second chamber. These ports are preferably made of flexible synthetic material and are inserted in holes in the material forming the remainder of the lid. Of course other constructions are possible, and they may be integral with the remained of the lid. An air vent 33 is also provided to allow ingress and egress of air while maintaining sterility of the chambers.

The lid provides a central portion 34 that is raised with respect to an outer portion 36, the two being connected in part by an intermediate wall 38. During decanting, the plasma passes over the bridge 20 and through a passage 40 between the bridge 20 and the wall 38. This passage thus directs the plasma into the second chamber.

The exterior of the lower surface of the first chamber may be provided with a foot 42 to facilitate resting the container on a table or other flat surface.

Preferably, the container is adapted to be held in a particular orientation in the frame of a centrifuge. In one embodiment, the helical shape of the floor 22 of the second chamber acts also as a cam to assist an operator in orienting the container in the frame. Preferably, however, a skirt 44 extends from the floor to provide this camming action and allow the two features to have different shapes specifically adapted to the particular purpose. In addition, a notch such as that shown at 46 is formed in the container between the upper ends of the floor 22, and that notch is designed to engage a similarly shaped element in the frame when the container is properly registered in the frame. The notch may be of various shapes and may include other features, such as a protuberance (not shown) that engages with a feature in the frame whereby containers having mostly common features may be distinguished from each other by the shape or configuration of the notch (e.g., width) or the presence of other features.

Figure 7:
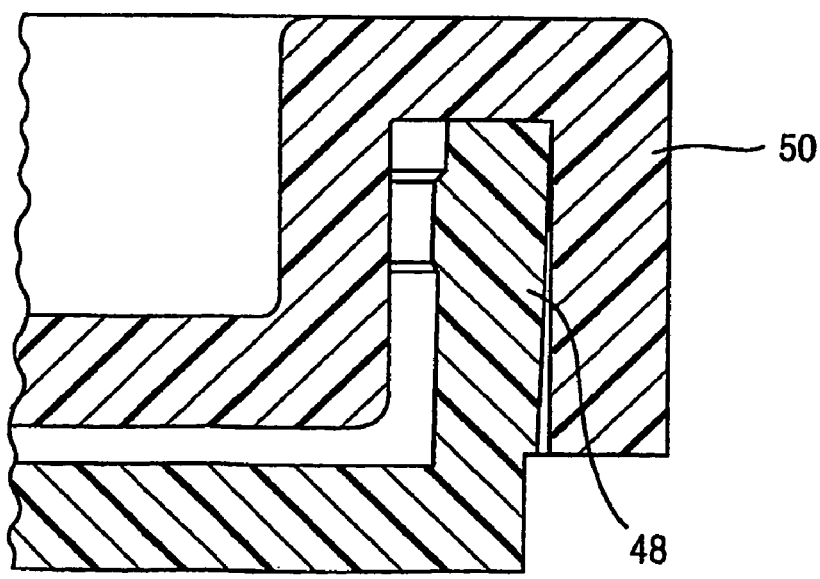
FIG. 7 is an enlarged detail of the portion of the container indicated in FIG. 2.

FIG. 7 shows the preferred engagement between the upper edge 48 of the base portion and the periphery 50 of the lid. Upper edge 48 extends upward and flares outward slightly to engage periphery 50 is a fluid tight seal. This engagement is such that the lid may be attached to the base without cements or glues.

Figure 8:
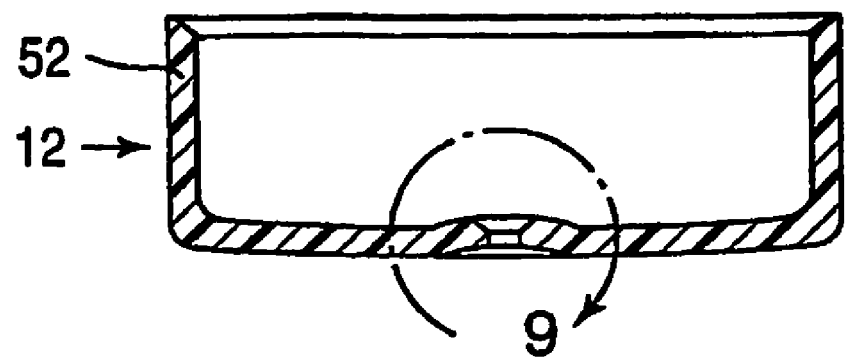
FIG. 8 is a transverse cross section of a preferred floating divider.
Figure 9:
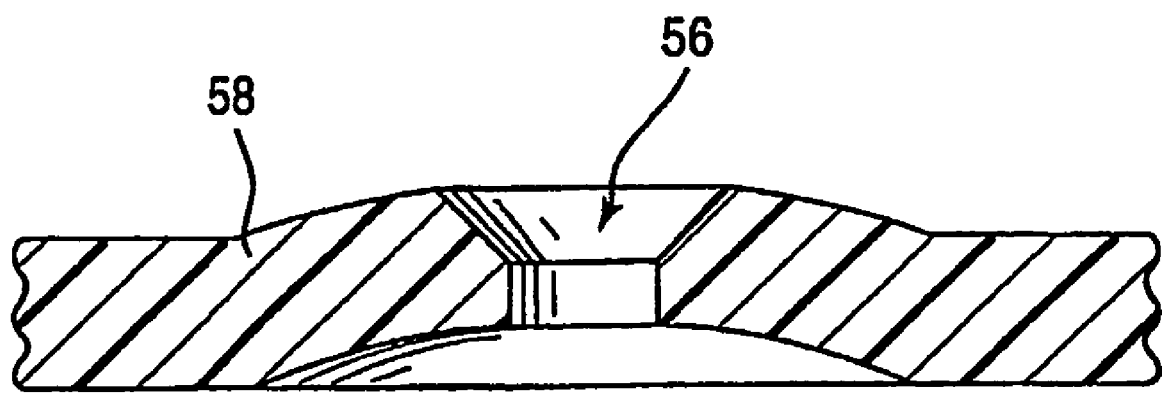
FIG. 9 is an enlarged detail of the portion of the divider indicated in FIG. 8.

FIGS. 8 and 9 illustrate a preferred floating divider. This divider is cup shaped and fits in the first chamber such that a small space is provided between the outer surface 52 of the divider and the inner surface of the wall 14 forming the first chamber. Preferably, the bottom of the divider is provided with an opening 56 to allow passage of components being separated. This opening may be formed in a raised portion 58 of the wall bottom 54. In the preferred embodiment, the diameter of the opening is approximately 0.058 inch and the raised portion 58 is raised by about 0.02 inch. The entrance to the opening is chamfered at about 135° to the horizontal.

Modifications within the scope of the appended claims will be apparent to those of skill in the art.

We claim:

1. A container comprising:
   a base portion forming a first chamber and a second chamber for retaining fluid and connected by a bridge that allows fluid in said first chamber to flow to said second chamber when said container is in a predetermined orientation;
   wherein said second chamber includes a narrow bottom portion and a helical floor portion at least partially surrounding said first chamber and arranged to direct said fluid to said bottom portion,
   a lid covering said first and second chambers that cooperates with said bridge to provide a passage for said fluid and including access means for providing sterile access to said first and second chambers,
   a floating divider in said first chamber configured to assume automatically a predetermined position in said first chamber with respect to components of said fluid when said fluid is undergoing centrifugal separation in said first chamber, and
   a cam surface for orienting the container when engaging a frame element of a centrifuge.

2. A container according to claim 1 wherein said cam surface comprises a skirt extending from the bottom of one of said chambers.

3. A container according to claim 1 wherein said cam surface comprises a helical skirt extending downward from one of said chambers.

4. A container according to claim 1 wherein said first and second chambers are connected by a bridge and said lid comprises a raised portion that covers said first chamber and a recessed portion that covers said second chamber and an intermediate wall that forms a passage with said bridge for receiving said fluid.

5. A container according to claim 1 wherein said access means comprises a first access port in said raised portion and a second access port in said recessed portion.

6. A container according to claim 1 wherein said floating divider is cylindrical and includes an opening allowing passage of fluids during centrifugation.

7. A container according to claim 6 wherein said floating divider includes a protuberance having said opening therein.

* * * * *